United States Patent
Shiba et al.

(10) Patent No.: US 10,458,939 B2
(45) Date of Patent: Oct. 29, 2019

(54) SENSOR COATED WITH RECEPTOR LAYER OF MIXTURE OF BASE MATERIAL AND PARTICULATE MATERIAL

(71) Applicant: NATIONAL INSTITUTE FOR MATERIALS SCIENCE, Ibaraki (JP)

(72) Inventors: Kota Shiba, Ibaraki (JP); Genki Yoshikawa, Ibaraki (JP); Gaku Imamura, Ibaraki (JP)

(73) Assignee: NATIONAL INSTITUTE FOR MATERIALS SCIENCE, Ibaraki (JP)

( * ) Notice: Subject to any disclaimer, the term of this patent is extended or adjusted under 35 U.S.C. 154(b) by 0 days.

(21) Appl. No.: 15/552,949

(22) PCT Filed: Feb. 25, 2016

(86) PCT No.: PCT/JP2016/055689
§ 371 (c)(1),
(2) Date: Aug. 23, 2017

(87) PCT Pub. No.: WO2016/136905
PCT Pub. Date: Sep. 1, 2016

(65) Prior Publication Data
US 2018/0017515 A1 Jan. 18, 2018

(30) Foreign Application Priority Data
Feb. 27, 2015 (JP) ................. 2015-038190

(51) Int. Cl.
*G01N 27/12* (2006.01)
*G01N 5/02* (2006.01)
(Continued)

(52) U.S. Cl.
CPC ............. *G01N 27/125* (2013.01); *G01N 3/00* (2013.01); *G01N 5/02* (2013.01); *G01N 21/00* (2013.01);
(Continued)

(58) Field of Classification Search
CPC ..... G01N 27/125; G01N 29/022; G01N 27/128
See application file for complete search history.

(56) References Cited

U.S. PATENT DOCUMENTS

| 2005/0090015 A1 | 4/2005 | Hartmann-Thompson |
| 2009/0011946 A1* | 1/2009 | Majumdar ........... G01N 33/542 506/9 |

(Continued)

FOREIGN PATENT DOCUMENTS

| CN | 102612638 | 7/2012 |
| EP | 1 278 061 | 1/2003 |

(Continued)

OTHER PUBLICATIONS

Daberkow et al., "Fluorescence labeling of colloidal core—shell particles with defined isoelectric points for in vitro studies" Acta Biomaterialia 8 (2012) 720-727. (Year: 2012).*

(Continued)

*Primary Examiner* — Dennis White
(74) *Attorney, Agent, or Firm* — Wenderoth, Lind & Ponack, L.L.P.

(57) ABSTRACT

As a receptor layer, a film of a composite material of a base material such as a polymer and particles that adsorb an analyte is used. When the present invention is applied to a surface stress sensor or the like, the Young's modulus of the receptor layer, which significantly affects detection sensitivity, can be preset with a high degree of freedom, by independently selecting particles that adsorb a desired analyte and a base material that disperses said particles therein.

14 Claims, 8 Drawing Sheets

(51) Int. Cl.
*G01N 29/02* (2006.01)
*G01N 29/036* (2006.01)
*G01N 3/00* (2006.01)
*G01N 21/00* (2006.01)
*B82Y 15/00* (2011.01)
*G01N 9/00* (2006.01)
*G01N 11/16* (2006.01)

(52) U.S. Cl.
CPC ......... *G01N 27/128* (2013.01); *G01N 29/022* (2013.01); *G01N 29/036* (2013.01); *B82Y 15/00* (2013.01); *G01N 9/002* (2013.01); *G01N 11/16* (2013.01); *G01N 2291/0255* (2013.01); *G01N 2291/0256* (2013.01); *G01N 2291/0257* (2013.01); *G01N 2291/02827* (2013.01); *G01N 2291/0427* (2013.01)

(56) References Cited

U.S. PATENT DOCUMENTS

| | | |
|---|---|---|
| 2009/0263287 A1 | 10/2009 | Hartmann-Thompson |
| 2010/0209301 A1 | 8/2010 | Hartmann-Thompson |
| 2011/0101996 A1 | 5/2011 | Potyrailo |
| 2013/0260983 A1 | 10/2013 | Omori et al. |
| 2014/0352447 A1 | 12/2014 | Yoshikawa et al. |

FOREIGN PATENT DOCUMENTS

| | | |
|---|---|---|
| EP | 1 529 804 | 5/2005 |
| EP | 2 664 599 | 11/2013 |
| GB | 2485059 | 5/2012 |
| JP | 62-47552 | 3/1987 |
| JP | 2000-283947 | 10/2000 |
| JP | 2005-134392 | 5/2005 |
| JP | 2007-51944 | 3/2007 |
| JP | 2009-103518 | 5/2009 |
| JP | 2013-227192 | 11/2013 |
| WO | WO-2005119233 A1 * | 12/2005 ............ B82Y 15/00 |
| WO | 2006/046509 | 5/2006 |
| WO | 2011/053234 | 5/2011 |
| WO | 2012/161256 | 11/2012 |
| WO | 2013/157581 | 10/2013 |

OTHER PUBLICATIONS

International Search Report dated May 10, 2016 in International Application No. PCT/JP2016/055689.
Genki Yoshikawa, "Mechanical analysis and optimization of a microcantilever sensor coated with a solid receptor film", Applied Physics Letters 98, 173502-1-173502-3 (2011).
Genki Yoshikawa et al., "Effects of Coating Materials on Two Dimensional Stress-Induced Deflection of Nanomechanical Sensors", Journal of Nanoscience and Nanotechnology, vol. 14, 2908-2912, 2014.
Kota Shiba et al., "Microfluidic syntheses of well-defined sub-micron nanoporous titania spherical particles", Chem. Commun., 6851-6853, 2009.
Kota Shiba, et al., "Preparation of Monodispersed Spherical Titania-Octadecylamine Particles Containing Silane-Coupling Reagents", Bulletin of the Chemical Society of Japan, Sep. 8, 2012, vol. 85, No. 9, p. 1040-1047.
Extended European Search Report dated Sep. 20, 2018 in corresponding European Application No. 16755649.7.
Office Action dated Aug. 21, 2018 in Japanese Application No. 2017-502484, with English translation.
Decision of Refusal dated Feb. 5, 2019 in corresponding Japanese Patent Application No. 2017-502484 with Machine translation.
Notification of Reasons for Refusal dated Dec. 4, 2018 in corresponding Japanese Application No. 2017-502484, with Machine translation.
First Office Action dated Apr. 19, 2019 in Chinese Patent Application No. 201680012175.1, with Machine Translation.
Communication pursuant to Article 94(3) EPC dated Jun. 17, 2019 in corresponding European Patent Application No. 16755649.7.

* cited by examiner

Fig. 3
AMINOPROPYL GROUP PARTICLES
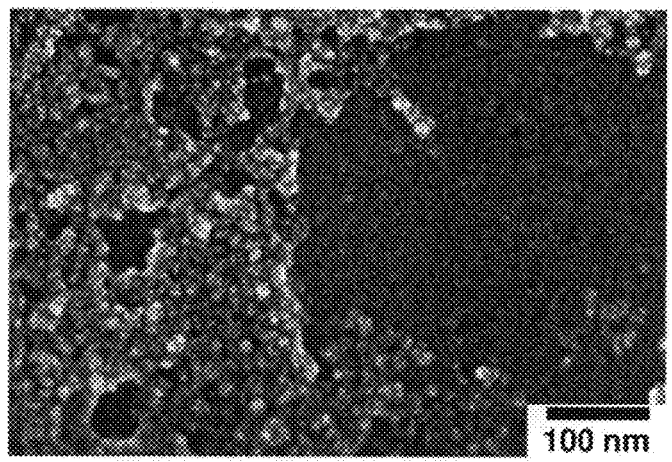
PHENYL GROUP PARTICLES
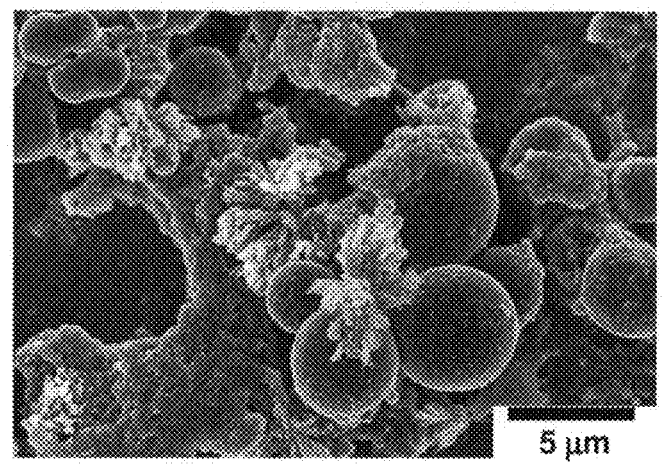
PARTICLES WITH NO MODIFYING GROUP
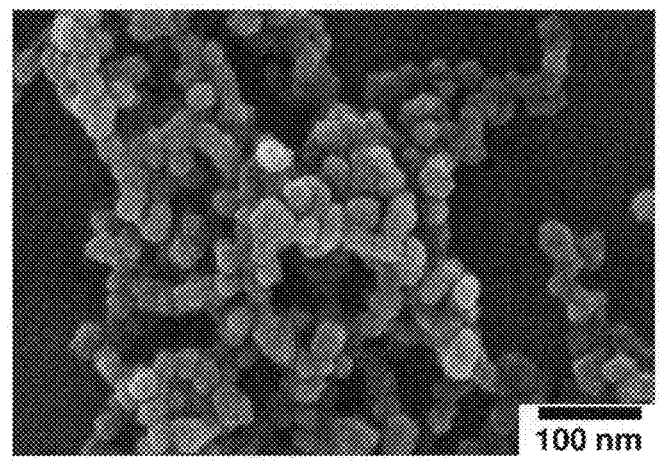

SENSOR COATED WITH RECEPTOR LAYER OF MIXTURE OF BASE MATERIAL AND PARTICULATE MATERIAL

TECHNICAL FIELD

The present invention relates to a sensor that enables selective detection with high sensitivity of a substance to be detected, by coating a surface of a sensor main body with a receptor layer in which a base material and a particulate material are mixed.

BACKGROUND ART

There are various kinds of sensors of a type such that changes in physical parameters which occur in accordance with adsorption of a molecule to be detected (a molecule of an analyte), and these sensors are used in various fields. In order to easily detect the changes in physical parameters, a sensor is generally coated with a layer called as "receptor layer", and then used for measurements. Since available receptor materials differ depending on physical parameters to be measured, various receptor layers optimized for each sensor have been developed. For example, there is a surface stress sensor that detects a stress that occurs in accordance with adsorption of a molecule of an analyte. For a receptor layer in this kind of sensor, various substances such as self-organized single molecule films, DNAs/RNAs, proteins, antigens/antibodies and polymers are used.

To improve the sensitivity of such sensor, it is effective to optimize the physical and chemical properties of the receptor layer in many cases. For example, regarding a surface stress sensor, as shown in Non-patent Literatures 1 and 2, it is reported that the Young's modulus and film thickness of a receptor material have significant effects. This tendency is represented by the following mathematical formula.

$$\Delta z = \frac{3l_c^2(t_f + t_c)}{(A+4)t_f^2 + (A^{-1}+4)t_c^2 + 6t_f t_c} \varepsilon_f \quad \text{[Mathematical Formula 1]}$$

$$A = \frac{[E_f w_f t_f (1 - v_c)]}{[E_c w_c t_c (1 - v_f)]}$$

The above-mentioned formula is for the cantilever-type surface stress sensor shown in Non-patent Literature 1. In the formula, $\Delta z$ is a deflection of the cantilever, $w_c$ is a width of the cantilever, $l_c$ is a length of the cantilever, $t_c$ is a thickness of the cantilever, $v_c$ is a Poisson's ratio of the cantilever, $E_c$ is a Young's modulus of the cantilever, $w_f$ is a width of the receptor layer, $t_f$ is a thickness of the receptor layer, $v_f$ is a Poisson's ratio of the receptor layer, $E_f$ is a Young's modulus of the receptor layer, and $\varepsilon_f$ is a distortion applied to the receptor layer. When sensitivity (in this case, a deflection amount of the cantilever) is calculated based on this mathematical formula, it is found that the sensitivity significantly depends on the Young's modulus of the receptor layer. Therefore, in order to attain high sensitivity, it is necessary to design a receptor layer having optimal values for physical parameters such as a Young's modulus. Based on the above-mentioned formula, the relationship between the Young's modulus and the deflection amount (sensitivity) is represented by a graph by using the film thicknesses of the receptor layer as parameters, and the graph is shown in FIG. 1. The calculations were conducted under the size of the cantilever of a length of 500 µm, a width of 100 µm and a thickness of 1 µm, and silicon as the material of the cantilever. The following matters are found from this graph.

A. When the film thickness is fixed, there is an optimal value in the Young's modulus of the receptor layer for the sensitivity of the surface stress sensor, and the sensitivity decreases at a Young's modulus that is either higher or lower than the optimal value, and B. When the thickness of the receptor layer is varied, the optimal Young's modulus changes. Specifically, the optimal Young's modulus is shifted to larger values and the sensitivity is also improved as the thickness of the receptor layer is decreased, whereas, conversely, the sensitivity tends to be not exerted in a region of small Young's moduli.

On the other hand, it is necessary to design a receptor layer specifically having chemical selectivity for this kind of sensor so as to selectively adsorb a molecule of an analyte. Specifically, it is necessary to design a functional group to be contained in the receptor layer and fix the functional group in the receptor layer in a stable state depending on the chemical property of the molecule of the analyte.

As mentioned above, in order to optimize sensitivity and selectivity, which are critically important two elements in a sensor of a type in which a molecule of an analyte is measured, it is generally necessary to optimize physical properties and chemical properties at the same time. However, any effective method by which such optimization is easily attained has not been established, and thus early attainment of such optimization is strongly demanded.

SUMMARY OF INVENTION

Technical Problem

The object of the present invention is to provide a method that achieves high performance by attaining selectivity of a molecule of an analyte derived from a chemical composition of a particulate material by using a receptor layer in which a base material, and the particulate material having different physical/chemical properties from those of the base material are mixed, while attaining physical properties that are different from those of the base material by forming a base material/particulate material composite by using a particulate material having different physical properties such as a Young's modulus.

Solution to Problem

The present invention is a sensor comprising: a receptor layer of a composite containing a base material and a particulate material, and a sensor main body having the receptor layer on a surface thereof so that the sensor detects a variation in a physical parameter caused on adsorption of a molecule of an analyte to the receptor layer.

Here, the physical parameter may be one or more kinds selected from a surface stress, a stress, a force, a surface tension, a pressure, a mass, an elasticity, a Young's modulus, a Poisson's ratio, a resonance frequency, a frequency, a volume, a thickness, a viscosity, a density, a magnetic force, a quantity of magnetism, an electric field, a magnetic flux, a magnetic flux density, an electric resistance, a quantity of electricity, a dielectric constant, an electric power, an electric field, an electric charge, an electrical current, an electric voltage, an electric potential, a mobility, an electrostatic energy, a capacitance, an inductance, a reactance, a susceptance, an admittance, an impedance, a conductance, a plasmon, a refractive index, a luminous intensity and a temperature.

Furthermore, the particulate material and the base material may have mutually different numerical values of a physical parameter.

Furthermore, the particulate material may be a nanoparticle.

Furthermore, the base material may be a polymeric material.

Furthermore, the polymeric material may be a polymer.

Furthermore, the particulate material may be a multicomponent material comprising a plurality of kinds of compounds.

Furthermore, the above-mentioned multicomponent particulate material may contain at least silica and titania.

Furthermore, the surface of the particulate material may be modified with one or more kinds of surface-modifying groups.

Furthermore, at least one of the surface-modifying groups may adsorb the molecule of the analyte.

Furthermore, the surface-modifying groups may comprise a hydrophobic surface-modifying group and a hydrophilic surface-modifying group.

Furthermore, the surface-modifying group may be fixed on the surfaces of the particles by co-precipitating a silane coupling agent with a raw material of the particulate material.

Furthermore, the surface-modifying group may be fixed by means of post-treatment of a surface of a previously synthesized particulate material with a silane coupling agent.

Furthermore, the surface-modifying group may be one or more kinds selected from an aminopropyl group, a phenyl group, an alkyl group, a mercaptopropyl group, a glycidyl group, a vinyl group, a sulfone group and a fluoro group.

Furthermore, the sensor main body may be a surface stress sensor.

Furthermore, the base material and the particulate material may have different Young's moduli from each other.

Advantageous Effect of Invention

According to the present invention, it becomes possible to attain high sensitivity and selectivity to various molecules of analytes, which have been difficult to attain by a single base material such as a polymer, by mixing particulate materials having different physical/chemical properties. More specifically, it becomes possible to control sensitivity and selectivity in a simultaneous and exhaustive manner by using, for example, one kind of polymer as a base material for a receptor layer, and adding particulate materials having different chemical compositions and Young's moduli to the base material. In other words, as shown in the curves of FIG. 1, since the Young's modulus can be varied freely within a very broad range by adding the particulate materials at any film thickness of the receptor layer (film of a base material), the sensitivity can be adjusted to an optional value along with each curve in FIG. 1 at any film thickness of the receptor layer (film of a base material). Furthermore, regarding the selectivity, by suitably selecting a particulate material having necessary functional groups and adding the particulate material to the base material according to the desired analyte, detectable analytes can be switched freely in a broad scope. By this way, not only it becomes unnecessary to modify the structure of the base material itself to a form that expresses affinity between the base material and the molecule of the analyte through various operations, as represented by an organic synthesis reaction, but also the process of reconsideration of conditions for the coating onto a surface of a sensor, which is necessitated in every change in the kind of the base material, can be omitted. Therefore, this is a significant advantage for not only practical realization at a laboratory scale but also practical realization at an industrial scale.

BRIEF DESCRIPTION OF DRAWINGS

FIG. 3 shows scanning electron microscope (SEM) images of the particulate materials having different surface-modifying groups prepared in Example 1.

DESCRIPTION OF EMBODIMENTS

Figure 1:
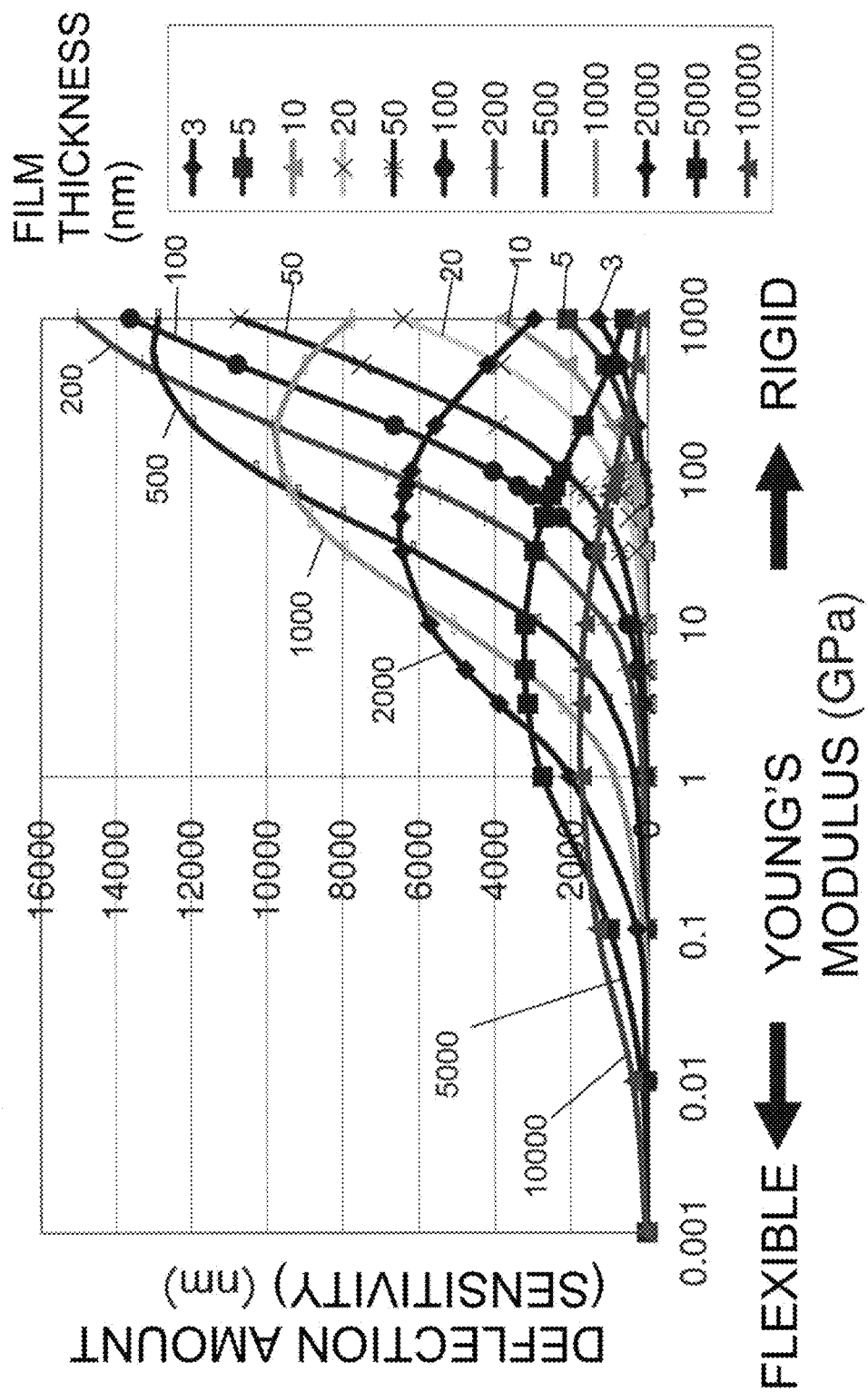
FIG. 1 is a drawing showing the relationship among the sensitivity, and the Young's modulus and film thickness of the receptor layer, for a surface stress sensor coated with a receptor layer.

The sensor of the present invention includes a receptor layer of a composite containing a base material and a particulate material (a base material/particulate material composite receptor layer) and a sensor main body having the receptor layer on the surface, which is configured to detect a change in a physical parameter which occurs when a molecule of an analyte is adsorbed by the receptor layer.

Specifically, the sensor main body may be any sensor main body that can detect a surface stress, a stress, a force, a surface tension, a pressure, a mass, an elasticity, a Young's modulus, a Poisson's ratio, a resonance frequency wave number, a frequency wave number, a volume, a thickness, a viscosity, a density, a magnetic force, a magnetic amount, an electric field, a magnetic flux, a magnetic flux density, an electric resistance, an amount of electricity, a dielectric constant, an electric power, an electric field, an electric charge, an electrical current, an electric voltage, an electric potential, a mobility, an electrostatic energy, a capacitance, an inductance, a reactance, a susceptance, an admittance, an impedance, a conductance, a plasmon, a refractive index, a luminous intensity and a temperature, and other various physical parameters, and the specific constitution of the sensor main body is not specifically limited.

This sensor detects the change in the physical parameter(s) caused in the receptor layer due to the adsorption of the molecule of the analyte on the receptor layer by the sensor main body. Therefore, the structure, operation and the like of the sensor main body that can be used in the present invention are not specifically limited as long as the sensor main body detects the change caused in the receptor layer due to the adsorption of the substance to be detected by the base material/particulate material composite receptor layer with which the surface of the sensor main body is coated. For example, in the case when a surface stress sensor is used, the substance to be detected is adsorbed by the base material/particulate material composite receptor layer with which the surface of the surface stress sensor is coated, the change in the stress caused in the receptor layer is detected, and the surface stress sensor outputs a signal. It should be noted that the term "adsorb" herein is used in the broadest meaning that encompasses not only physical adsorption but also chemical bonding and adsorption by biochemical actions. Furthermore, the composite used in the receptor layer may be composed of only the base material and the particulate substance, or may be composed of other auxiliary components (for example, components that improve the dispersibility of the particles, modifiers for exerting any physical/chemical properties that are difficult to achieve by only the base material component, and the like) may also be added. The base material itself may be composed of plural substances (for example, plural kinds of polymers).

Furthermore, the thickness (film thickness) of the receptor layer on the surface of the sensor main body can be suitably designed with consideration for the detection sensitivities of the various physical parameters and the like, and for example, a range of 1 nm to 1,000 μm can be exemplified. In addition, when considered based on FIG. 1, when the film thickness of the receptor layer is in the range from 100 nm to 10 μm, it is possible to maximize the deflection of the cantilever within the range of the Young's modulus of a generally-used material (1 MPa to 1,000 GPa). Furthermore, the Young's modulus may be lower than 1 MPa in the case when the receptor layer is constituted by a material containing very many voids, but in such case, it is preferable that the film thickness of the receptor layer is within the range of 100 nm to 1,000 μm from the viewpoint of maximization of the deflection of the cantilever.

The particulate material used for the base material/particulate material composite receptor layer in the present invention may have any shape and structure as long as the particulate material satisfies the assumed condition that the particulate material has different physical/chemical properties from that of the base material such as a polymer. The particle size of the particulate material may be any particle size such that the particulate material can be dispersed in the base material and is not specifically limited, and nanoparticles are preferable because physical properties as a bulk are easily defined and a quantitative discussion can be made. The nanoparticles herein refer to particles having a particle size of 1 nm to 100 nm.

The shape of each particle of the particulate material may be either isotropic or anisotropy. The structure of each particle may be a dense structure, a non-dense structure such as porous or hollow, or a core-shell type structure. Furthermore, one or more kinds of optional surface-modifying group(s) can be suitably fixed on the surface of the particulate material depending on a molecule of an analyte to be detected. For example, in the case of a particulate material having two or more kinds of surface-modifying groups, it is preferable that the particulate material includes hydrophobic surface-modifying group(s) and hydrophilic surface-modifying group(s). Furthermore, it is preferable that at least one of the surface-modifying groups among the surface-modifying groups adsorbs a molecule of an analyte.

Furthermore, for example, the surface-modifying groups can be fixed on the surfaces of the particles by co-precipitating the silane coupling agent with the particulate material raw material, or can be fixed by subjecting the surfaces of the particulate material that has been synthesized in advance to a post-treatment with the silane coupling agent. Furthermore, the surface-modifying groups may be combined with polymers or bio-related molecules, in addition to molecules having a thiol group, phosphonic acid and the like.

As such surface-modifying groups, for example, one or more kinds of an aminopropyl group, a phenyl group, an alkyl group, a mercaptopropyl group, a glycidyl group, a vinyl group, a sulfone group and a fluoro group can be exemplified.

The substance that constitutes the particles of the particulate material may be any substance as long as the condition that the substance has different physical/chemical properties from those of the base material. For example, simple substance such as metals, or compounds such as oxides and sulfides, inorganic-organic hybrids, and the like can be preferably exemplified. Furthermore, it is preferable that the particulate material is a multicomponent material composed of plural kinds of compounds such as silica and titania.

In addition, in the case when the present invention is applied to a surface stress sensor such as MSS, when the base material is a soft material such as a polymer, it is desirable that the Young's modulus of the particles is higher than that of the base material. Conversely, in the case when the base material is a substance that is hard to some extent, it is sometimes desirable to use a material, such as polymer particles and air bubbles, that decreases the Young's modulus of the entire composite receptor layer. That is, it is preferable that the particulate material and the base material have different values of physical parameters from each other.

Furthermore, the above-mentioned particulate material may be synthesized by any technique. Specifically, the technique is not specifically limited, and ranges from a precipitation reaction in a homogeneous solution, a reaction in a pseudo-homogeneous system utilizing an emulsion, a reaction in a vapor phase utilizing spray drying or thermal decomposition, to solid phase reactions such as ball milling.

As an example of the sensor main body coated with the base material/particulate material composite receptor layer, a surface stress sensor is exemplified, but the shape, material, size and the like thereof are not specifically limited, and any object can be used. For example, a slice-like element supported at one portion or plural portions can be preferably exemplified. Furthermore, for example, sensor main bodies having various forms such as slice-like objects supported at two or more portions such as a double-supported beam, membrane bodies and the like can be adopted.

The technique for coating the sensor surface with the base material/particulate material composite receptor includes, but is not specifically limited to, dip coating, spray coating, spin coating, inkjet spotting, casting, coating using a doctor blade, and the like.

Furthermore, if the particulate material used as the receptor layer efficiently adsorbs a desired molecule of the analyte by itself, such particulate material can be used in its original form. Alternatively, the detection performance can be improved by modifying the particulate material with specific surface-modifying groups so that the particulate material adsorbs a desired molecule of the analyte, improving the adsorption efficiency, or increasing the selectivity of the substance to be adsorbed, or the like. Furthermore, the modification by the surface-modifying groups can be conducted for the purposes that do not directly relate to adsorption of the molecule of the analyte, for example, improvement of the durability, environment resistance and the like of a sensor coated with the base material/particulate material composite, such as mutual bonding of the particles and tackiness with a substrate.

Meanwhile, it is considered that there are considerably many cases when the major part or entirety of the surface of the particulate material is coated with the base material in the base material/particulate material composite layer. Even in these cases, in the case when the base material is a polymer or the like, the molecule of the analyte can permeate through the coating of the base material and easily reach the particulate material. Alternatively, even a base material through which the molecule of the analyte is difficult to permeate is used, in the case when the coating thickness is extremely thin, or pinholes or the like with a number/size sufficient for coating are present, the molecule of the analyte can also easily reach the particulate material. Therefore, it is desirable to suitably adjust the base material and particulate material used, the mixing ratio of the material and particulate material in a coating body, the thickness of a coating body layer, additives to the base material, and the like according to the molecule of the analyte, the necessary detection sensitivity, and the environment for use, and the like.

Regarding the selectivity, it should be noted that it is also possible to utilize the selectivity of the base material itself due to the functional groups and the like in the base material and the selectivity possessed by the particulate material in combination. For example, in the case when a composite layer in which a base material having hydrophobic functional groups is mixed with a particulate material having hydrophilic functional groups is utilized, it becomes possible to efficiently adsorb amphipathic compounds.

EXAMPLES

The present invention will further be explained below in detail based on Examples. However, as a matter of course, the present invention is not limited to these Examples.

Example 1

MSS Coated with PVP/Silica-Titania Hybrid Particulate Material Composites Having Various Surface-Modifying Groups In the following, an example of measurement by using sensors obtained by forming particulate materials having various surface-modifying groups and a polymer as a base material into composites, and coating the sensors with the composites as receptor layers, will be explained.

Figure 2:
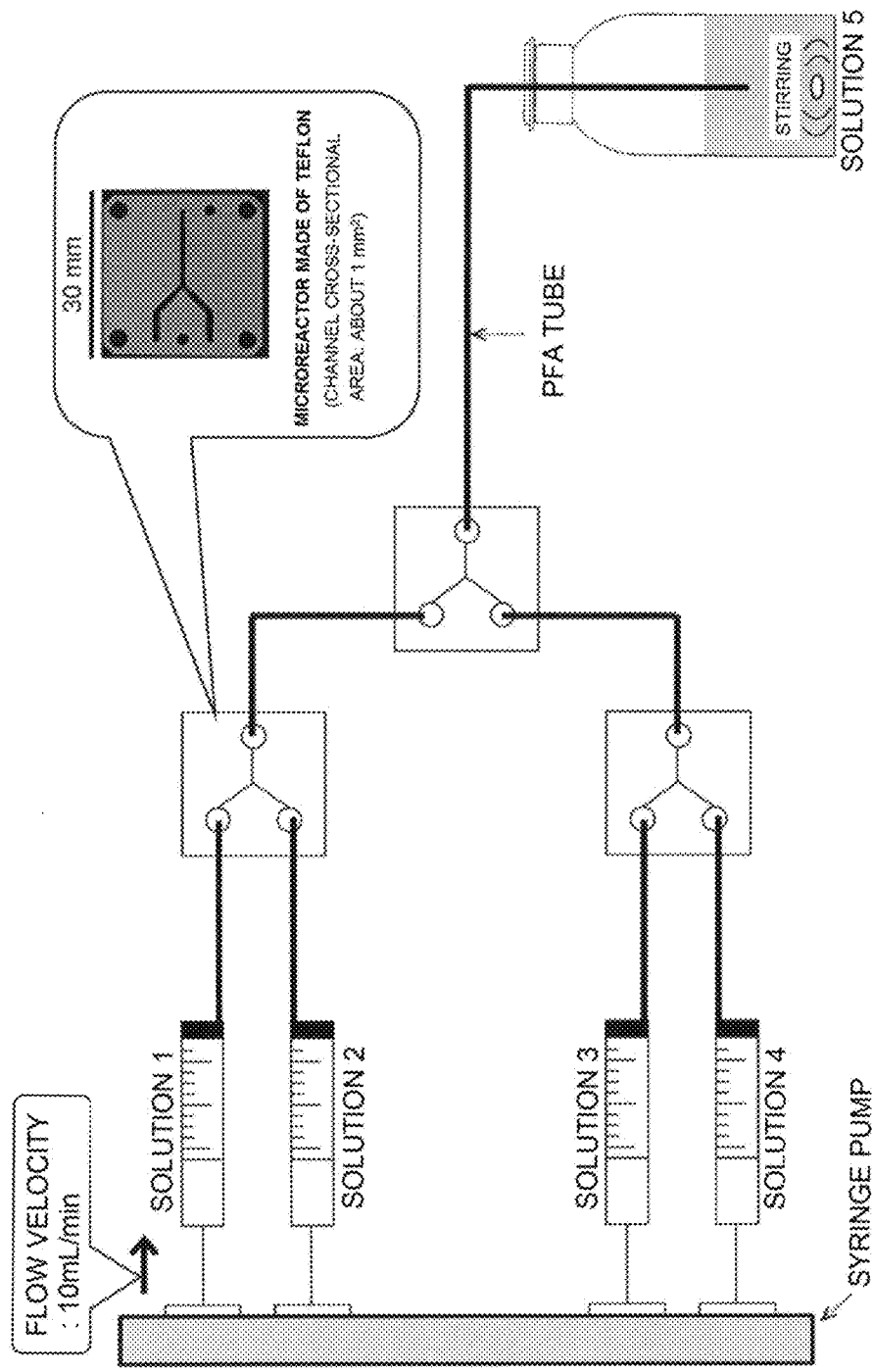
FIG. 2 is a drawing showing an example of the constitution of the apparatus utilized for the synthesis of the particulate materials in Example 1.

The above-mentioned silica-titania hybrid particulate materials having various surface-modifying groups were each synthesized by co-hydrolysis and a condensation polymerization reaction of silicon tetraethoxide or various silane coupling agents and titanium tetraisopropoxide (TTIP) in an ammonia basic isopropanol (IPA) aqueous solution in which octadecylamine (ODA) was dissolved. As the silane coupling agent, 3-aminopropyltriethoxysilane and phenyltriethoxysilane were used. The above-mentioned synthesis reaction was conducted by using a microreactor made of Teflon (registered trademark) having a Y-shaped flow path of a size of micrometers (FIG. 2) (Non-patent Literature 3). Four precursor solutions: Solution 1: silicon alkoxide or various silane coupling agents/IPA, Solution 2: $H_2O$/IPA/ammonia, Solution 3: TTIP/IPA, Solution 4: $H_2O$/IPA were used, and the solutions from Solution 1 to Solution 4 were prepared at unified volumes. The precursor solutions were flowed simultaneously at a predetermined flow rate by a syringe pump. Solution 1 and Solution 2, Solution 3 and Solution 4 were respectively mixed in microreactors disposed in parallel, and the solutions ejected from the two reactors were further mixed in another microreactor to give one reaction solution. The reaction solution was ejected into a precursor solution 5: ODA/$H_2O$/IPA, which had been separately prepared in advance, and stirred at a predetermined velocity until the ejection was completed. Thereafter, the mixture was allowed to stand still at room temperature, whereby the above-mentioned particulate material dispersion liquid was obtained. The images of the particles observed under an SEM are shown in FIG. 3.

The particulate material synthesized in this Example is silica-titania hybrid particles having an aminopropyl group or a phenyl group, or silica-titania hybrid particles having no specific functional group, depending on the kind of the alkoxide or silane coupling agent used during the synthesis. However, it should be noted that all of these three kinds of particulate materials were synthesized in the presence of ODA, and thus the particle structure includes an octadecyl group.

As the polymer to which the above-mentioned particulate material is added, polyvinyl pyrrolidone (PVP), which is a kind of common polymer, was used here. By mixing predetermined amounts of PVP, the above-mentioned particle dispersion liquid, water and IPA, preparation was conducted so that both of the PVP concentration and the particle concentration became 1 g/L. The product was ultrasonicated, the dispersion of the particles was confirmed by visual observation, and the product was immediately sprayed and dried on a sensor chip by using a spray coater. As the sensor, a piezo resistive MSS having a membrane type structure suggested in Patent Literature 1 was used.

Figure 4:
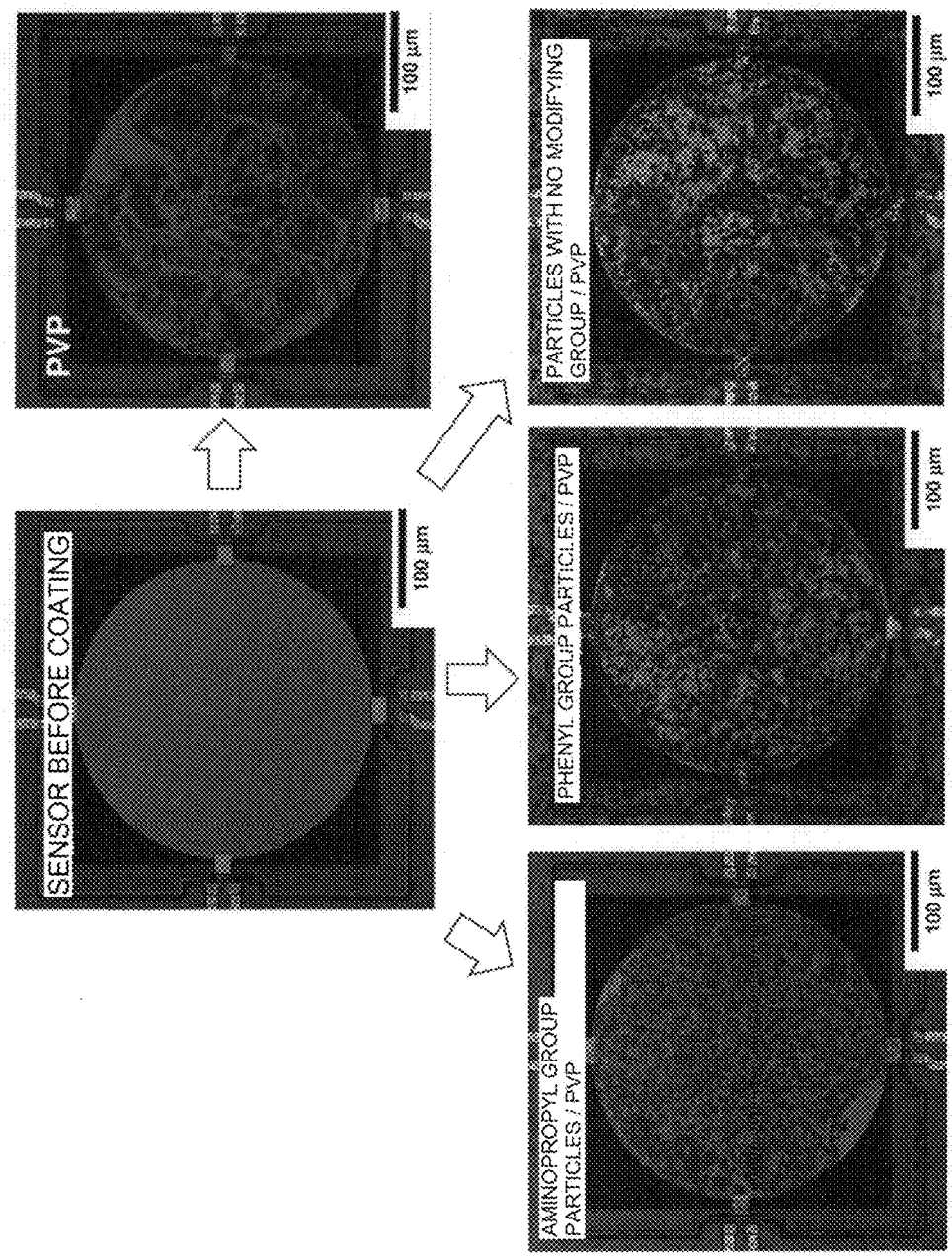
FIG. 4 shows optical microscope images before and after adding the particulate material of Example 1 to polyvinylpyrrolidone (PVP), and coating the surface of a membrane-type surface stress sensor (MSS) with the particulate material.

The optical microscope images of the MSS coated with the PVP/silica-titania hybrid particulate material composite, which were prepared in this Example, are shown in FIG. 4. By comparing with the MSS before the coating, it can be confirmed that the entirety of the film structure was coated.

Figure 5:
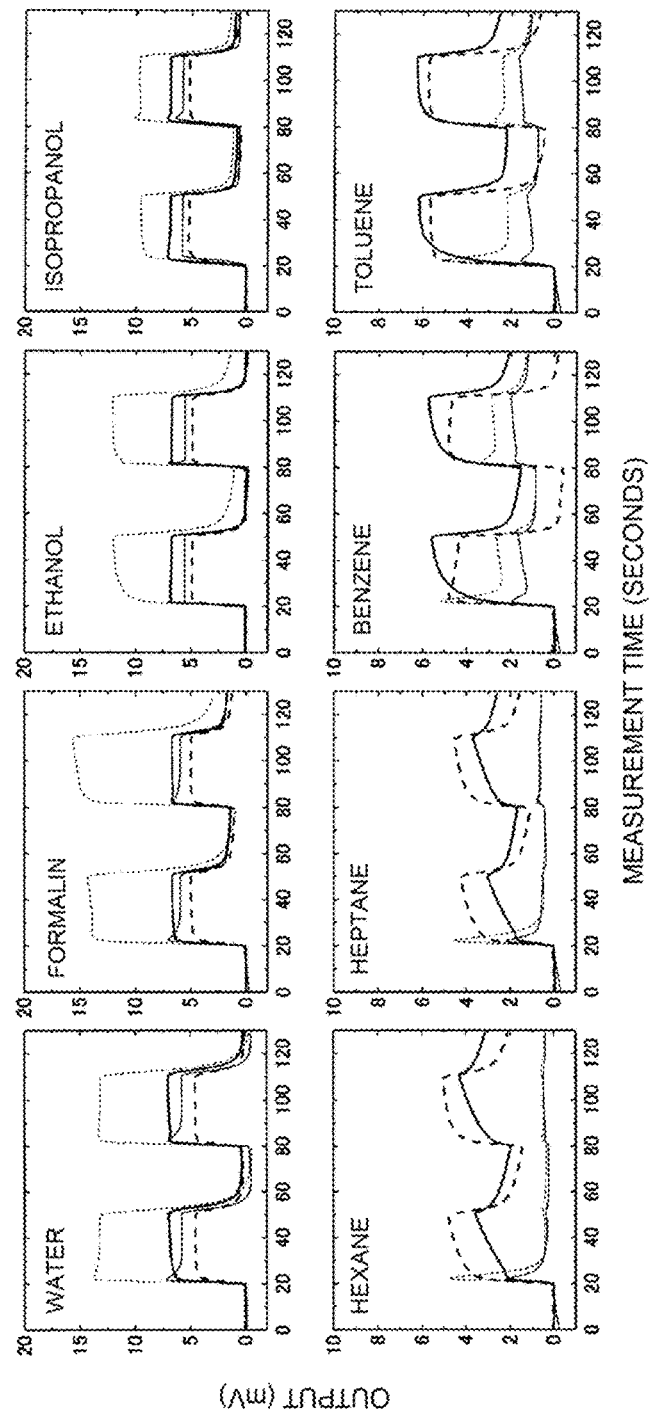
FIG. 5 is a drawing showing the results of the measurements of eight compounds by using the PVP/particulate material composite-coated MSS of Example 1 and a PVP-coated MSS for comparison.
Figure 6:
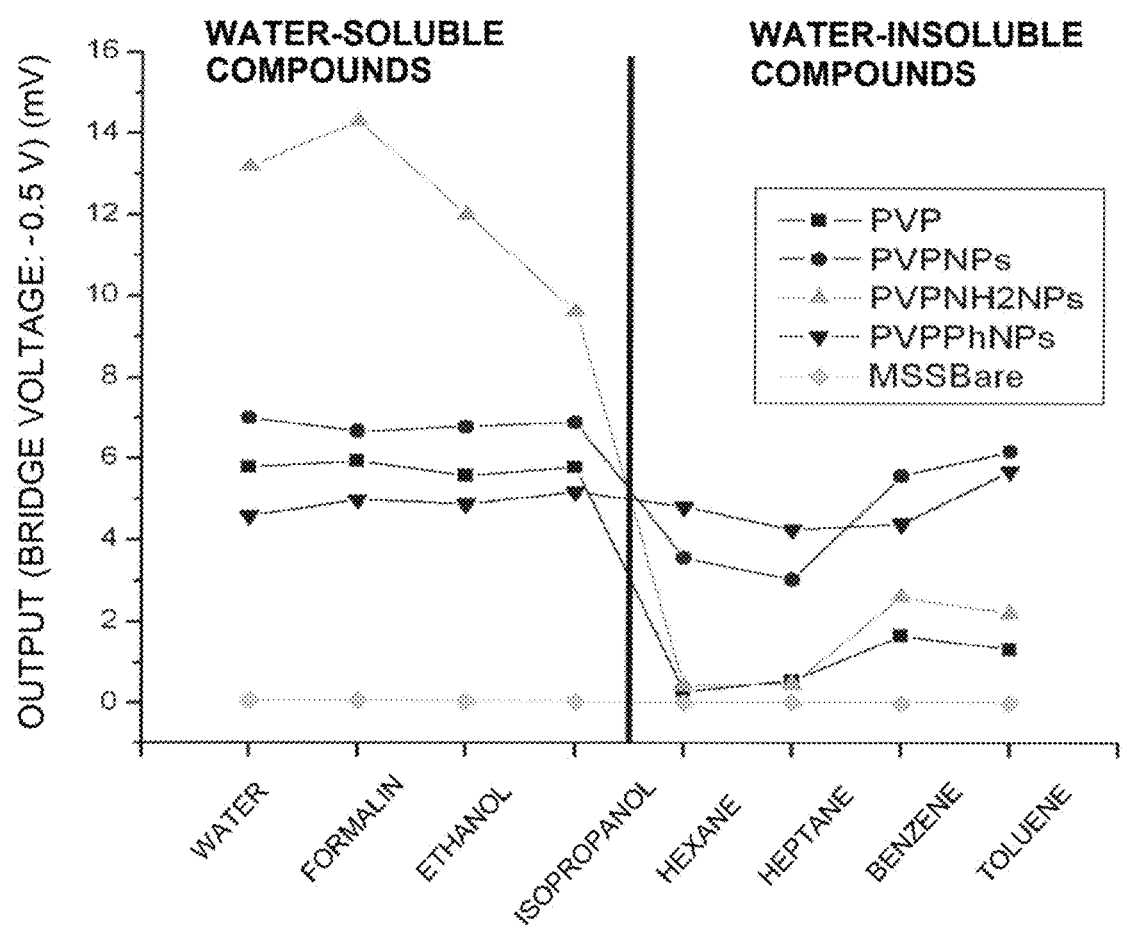
FIG. 6 is a drawing in which the values of the sensor signals of FIG. 5 at around 30 seconds (just before switching to a purge gas) after the injection of a sample gas was extracted, and the values were plotted for every measured compound.

Subsequently, water and water-soluble/insoluble chemical species were measured. Specifically, eight kinds of chemical species: water, formaldehyde (formalin), ethanol, IPA, hexane, heptane, benzene and toluene were each taken into a vial, and nitrogen as a carrier gas was flown into the vial at 100 mL/min, whereby the chemical species was introduced as a gas containing a certain amount of sample vapor into a tightly-closed chamber in which MSS was housed. The results of the measurements of the respective samples are shown in FIGS. 5 and 6. As objects for comparison, a result obtained by coating a piezo resistive MSS having an identical structure with PVP (a 1 g/L solution) by using an identical spray coater, and conducting a measurement, and a result obtained by conducting a measurement by using an MSS with no coating are also shown in FIGS. 5 and 6 (the result of the measurement using the MSS with no coating ("MSS bare" in the drawing) is shown in only FIG. 6). In FIG. 6, "PVP" represents a sensor coated with only PVP with no particulate material, "PVPNPs" represent sensors coated with a PVP containing PVP with no surface-modifying group, "PVPNH2NPs" represent sensors coated with a PVP containing a particulate material modified with an aminopropyl group, and "PVPPhNPs" represent sensors coated with a PVP containing a particulate material modified with a phenyl group.

In the case of the coating with only PVP ("PVP" in FIG. 6), the sensor responded to the water-soluble compounds, but responded faintly to the water-insoluble compounds. This can be explained by that the PVP itself is a water-soluble polymer. It is found that, in the case when the phenyl group-modified particles were added ("PVPPhNPs" in FIG. 6), the response to the water-soluble compounds was approximately the same, whereas the response to the water-insoluble compounds was improved. The relative signal intensity with respect to the signal intensity of the response to water is 1 or more for all of the four kinds of water-insoluble compounds, and this is considered to be the effect of the introduction of the hydrophobic phenyl groups. The response to the four kinds of the water-insoluble compounds was improved also in the cases of the silica-titania hybrid particles having no specific modifying groups, and this is considered to be due to the presence of the hydrophobic octadecyl group in the structure. On the other hand, in the case when the particles modified with the hydrophilic aminopropyl group were added ("PVPNH2NPs" in FIG. 6), the response to the water-soluble compounds was significantly improved. As mentioned above, it was shown that the molecule of the analyte selectivity of the receptor layer can be controlled depending on the surface property of the added particulate material.

Example 2

Preparation of High Young'S Modulus Composite and Improvement of Sensitivity of MSS by Addition of Silica-Titania Hybrid Particulate Material to PVP As is understood from the optical microscope images in FIG. 4, in the case when the particles modified with an aminopropyl group were added, the entirety of the surface of the sensor is coated in a relatively homogeneous manner. Therefore, in order to discuss the effect of the Young's modulus of the composite here, the case when particles modified with an aminopropyl group were added will be considered.

The Young's moduli of silica and titania are about 70 GPa and about 200 GPa, and in the case of the hybrid particles used in this Example is considered, the Young's modulus of the hybrid particles is assumed to be around 100 GPa with consideration for a weighted average based on a weight ratio of silica and titania calculated from the raw materials for the preparation of the particles. Based on that the Young's modulus of PVP is about 2 GPa, the Young's modulus of the PVP/particulate material composite receptor layer in this Example can be estimated to be approximately 50 GPa. The film thickness of the composite coating was estimated to be approximately 100 to 200 nm by a film thickness meter. According to Non-patent Literature 1, for the sensitivities when the Young's modulus is 2 GPa and 50 GPa, the latter sensitivity tends to be several times larger in the case when the sensitivities are compared at a film thickness of 100 to 200 nm (see also FIG. 1, which shows the relationship between the Young's modulus and sensitivity using film pressures as parameters). As is apparent from FIGS. 5 and 6, for example, the sensitivities against the water-soluble compounds are approximately twice or more, and thus the contribution of the Young's modulus is suggested.

Figure 7:
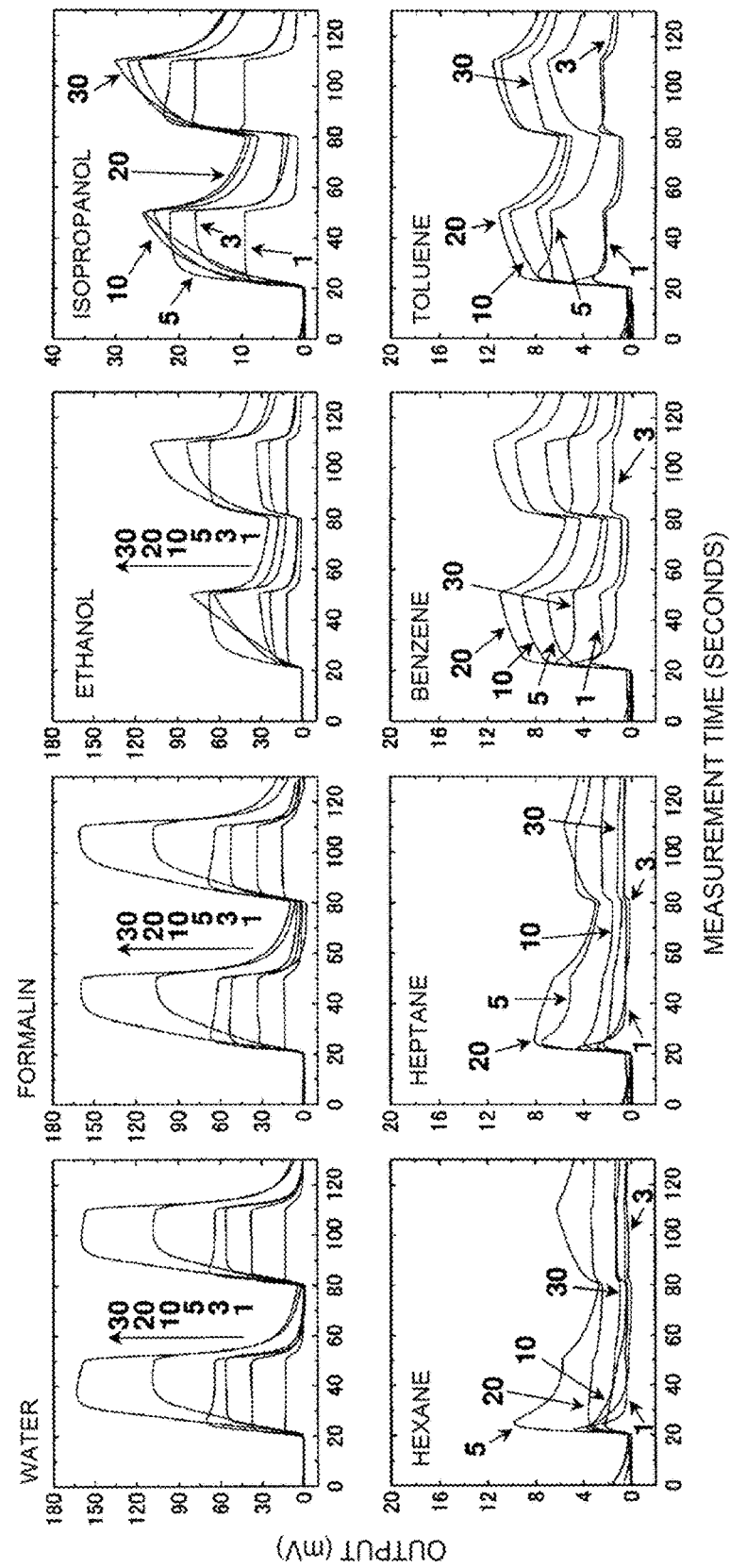
FIG. 7 is a drawing showing the result of the measurements of eight kinds of compounds by using a PVP/particulate material composite-coated MSS, which is similar to that of Example 2 except for the number of coatings.
Figure 8:
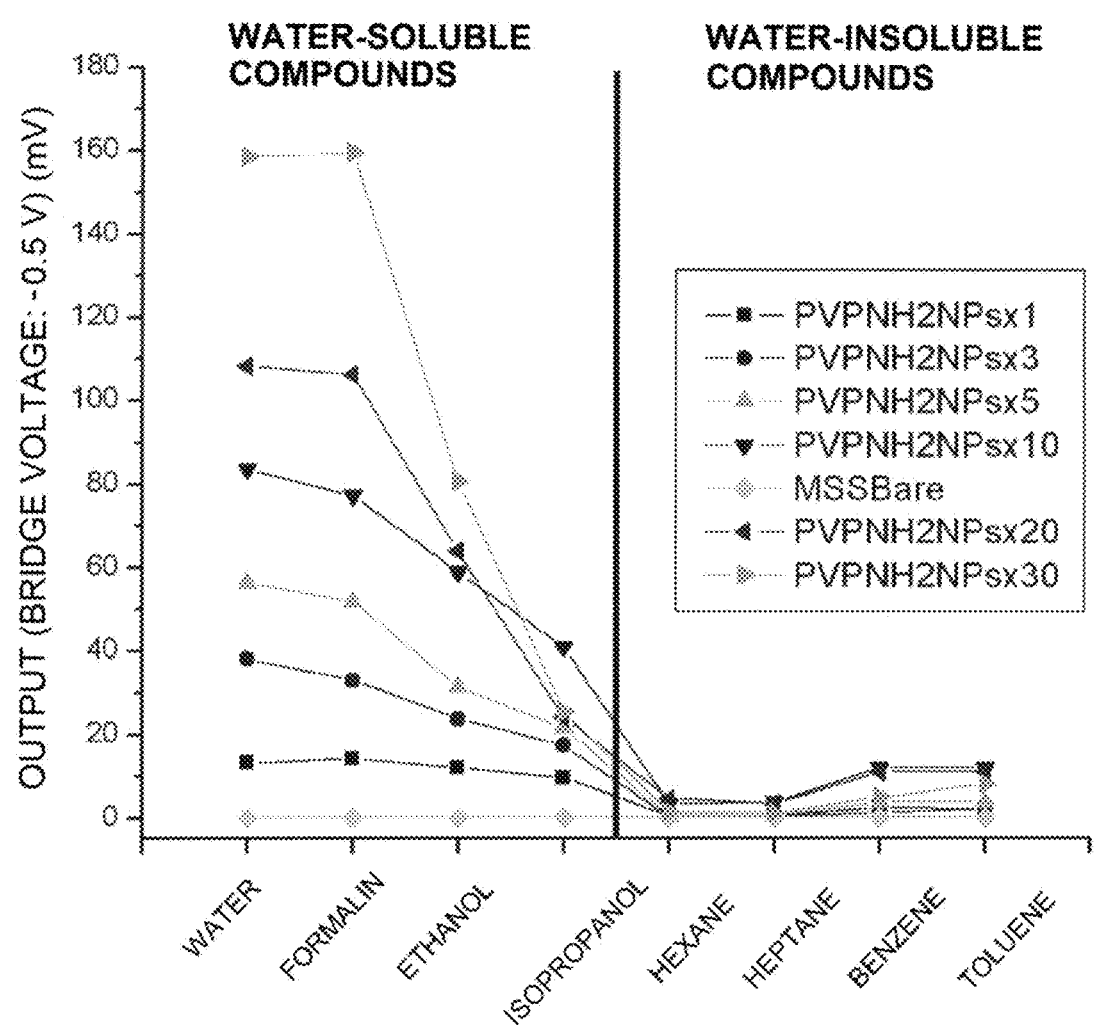
FIG. 8 is a drawing in which the values of the sensor signals of FIG. 7 at around 30 seconds (just before switching to a purge gas) after the injection of a sample gas was extracted, and the values were plotted for every measured compound.

Subsequently, in order to confirm whether or not there is a tendency that the sensitivity increases in accordance with the increase in the film thickness as shown in Non-patent Literature 1, the surface of the sensor was repeatedly coated with the above-mentioned PVP/aminopropyl group-modified particulate composite, and the above-mentioned eight kinds of chemical species were measured. The results are shown in FIGS. 7 and 8. "PVPNH2NPs" in FIG. 8 represents sensors each coated one or more times (×1 to 10) with a PVP containing a particulate material modified with an aminopropyl group, and "PVPPhNPs" represents sensors each coated 20 times (×20) or 30 (×30) with PVP containing a particulate material modified with a phenyl group.

Regarding water and formaldehyde, a tendency that the sensitivity increased in accordance with the increase in film thickness was observed. On the other hand, as the hydrophobicity of the compound became strong, for example, as the alkyl chain became longer, a simple tendency of increase in sensitivity was not observed. More specifically, decrease in sensitivity was confirmed from the case when spray coating was conducted about 10 or 20 times. According to Non-patent Literature 1, a film thickness that gives a maximum sensitivity is present in the case when the Young's modulus is constant, and it can be interpreted that the result in the present case follows such tendency.

In addition, when FIG. 1 is referred to, it is understood that a receptor layer having a smaller film thickness and a larger Young's modulus is more advantageous in achieving high sensitivity. However, since a material having a high Young's modulus, i.e., a stiff material, generally tends to allow less absorbance/permeation of an analyte, high sensitivity cannot always be achieved by using a material having a high Young's modulus. For example, if a diamond film is used, a film having a very large Young's modulus can be attained, but an analyte cannot enter into this film. As a result, little strain is induced in a receptor layer using diamond as a base material, and thus the detection sensitivity is extremely low. Therefore, in principle, high detection sensitivity can be achieved if a base material that can increase the Young's modulus and decrease the film thickness and easily permeates and absorbs an analyte can be used; however, it is advantageous to use a polymer as a base material since it is easy to actually handle as a base material, and from the viewpoint of functionalization of a versatile material.

On the other hand, the reason why the sensitivity still tends to increase in the measurement of water and formaldehyde is expected to be the contribution of a chemical interaction with the receptor surface which cannot be explained based on only the physical parameters such as Young's modulus and film thickness.

Furthermore, by modifying the surface of the particulate material with both a hydrophilic surface-modifying group and a hydrophobic surface-modifying group that is longer than this hydrophilic surface-modifying group, the surface can be made macroscopically hydrophobic but microscopically hydrophilic. For example, the surface of the particle modified with an aminopropyl group prepared in this Example was surface-modified with an octadecyl group in addition to an aminopropyl group; when the surface of the particulate material is in such state, the surface is macroscopically hydrophobic due to the presence of the octadecyl group having a long chain length, but many sites that adsorb water are microscopically present due to the co-existence of the aminopropyl group. By this way, a state that water in a bulk-shape such as a liquid state is repelled, whereas water vapor (in other words, water molecules in a state that they are dispersed in a gas, which are not bulk-like water) is adsorbed, is attained.

Based on that an octadecyl group and an aminopropyl group have chain lengths of about several angstroms to 1 nm, it is considered that only a molecule of an analyte can be adsorbed so as to be selectively removed from water, for example, by disposing the aminopropyl group particles/PVP-coated MSS of this Example in water in which molecules having affinity for amino groups (proteins and the like) are dissolved. Accordingly, not only measurements in gases, but also measurements in liquids which have not been achieved until now, such as direct measurements of concentrations of various gases in blood, can be attained.

The reason why the hydrophilic functional groups and the hydrophobic functional groups can be present in a periodically or approximately periodically mixed manner on the surfaces of the aminopropyl group/octadecyl group surface-modified particles of this Example is that these particles are silica-titania hybrid nanoparticles, and silica parts and titania parts to which the respective functional groups are bonded repeatedly emerge on the surfaces thereof. In order to produce particles in which plural kinds of materials repeatedly emerge on the surfaces in such way, it is only necessary to mix and react plural kinds of alkoxides in the presence of organic substances as shown in Example 1. Furthermore, in order to control the size and shape of the particles produced by this reaction, for example, it is only necessary to use a technique of flow synthesis as in Example 1.

In either case, it was shown that it is possible to increase sensitivity by controlling the physical parameter (the physical parameter herein is Young's modulus) of a receptor layer, which is the object of the present invention.

INDUSTRIAL APPLICABILITY

As explained above in detail, according to the present invention, it becomes possible to achieve high sensitivity and selectivity by using a base material/particulate material composite as a receptor layer material to thereby attain the physical/chemical properties of the receptor layer that affect measurements at a far higher degree of freedom than that in the case when a receptor layer is constituted singly by a base material. Therefore, it is expected that the present invention greatly contributes to the field of sensors in which a receptor layer is disposed on a surface of a sensor main body.

CITATION LIST

Non-Patent Literature

Non-patent Literature 1: G. Yoshikawa, "Mechanical Analysis and Optimization of a Microcantilever Sensor Coated with a Solid Receptor Film," Appl. Phys. Lett. 98, 173502-1-173502-3 (2011).
Non-patent Literature 2: G. Yoshikawa, C. J. Y. Lee and K. Shiba, "Effects of Coating Materials on Two Dimensional Stress-Induced Deflection of Nanomechanical Sensors," J. Nanosci. Nanotechnol. 14, 2908-2912 (2013).
Non-patent Literature 3: K. Shiba and M. Ogawa, "Microfluidic syntheses of well-defined sub-micron nanoporous titania spherical particles," Chem. Commun. 6851-6853 (2009).

The invention claimed is:

1. A sensor comprising:
a receptor layer of a composite containing a base material and a particulate material, and
a sensor main body having the receptor layer on a surface thereof so that the sensor detects a variation in a physical parameter caused on adsorption of a molecule of an analyte to the receptor layer,
wherein the particulate material is a multicomponent material comprising a plurality of compounds,
wherein the surface of the particulate material is modified with one or more surface-modifying groups, and at least one of the surface-modifying groups adsorbs the molecule of the analyte,
wherein the sensor main body is a surface stress sensor, and
wherein the physical parameter is a surface stress.

2. The sensor according to claim 1, wherein the particulate material and the base material have mutually different numerical values of a physical parameter.

3. The sensor according to claim 1, wherein the particulate material is a nanoparticle.

4. The sensor according to claim 1, wherein the base material is a polymeric material.

5. The sensor according to claim 4, wherein the polymeric material is a polymer.

6. The sensor according to claim 1, wherein the multicomponent particulate material comprises silica and titania.

7. The sensor according to claim 1,
wherein the one or more surface-modifying groups of the particulate material are different from the base material.

8. The sensor according to claim 7, wherein the surface-modifying groups comprise a hydrophobic surface-modifying group and a hydrophilic surface-modifying group.

9. The sensor according to claim 7, wherein the surface-modifying group is fixed on the surfaces of the particles by co-precipitating a silane coupling agent with a raw material of the particulate material.

10. The sensor according to claim 1, wherein the surface-modifying group is fixed by means of post-treatment of a surface of a previously synthesized particulate material with a silane coupling agent.

11. The sensor according to claim 7, wherein the surface-modifying group is one or more selected from the group consisting of an aminopropyl group, a phenyl group, an alkyl group, a mercaptopropyl group, a glycidyl group, a vinyl group, a sulfone group and a fluoro group.

12. The sensor according to claim 1, wherein the base material and the particulate material have different Young's moduli from each other.

13. The sensor according to claim 6, wherein the multicomponent particulate material comprises silica-titania hybrid nanoparticles.

14. The sensor according to claim 6, wherein the multicomponent particulate material comprises silica-titania hybrid nanoparticles having functional groups, and a silica part and a titania part to which respective functional groups are bonded repeatedly emerge on a surface thereof.

* * * * *